April 5, 1932.
L. BURBANK
Plant Pat. 14
PLUM
Filed Sept 23, 1930
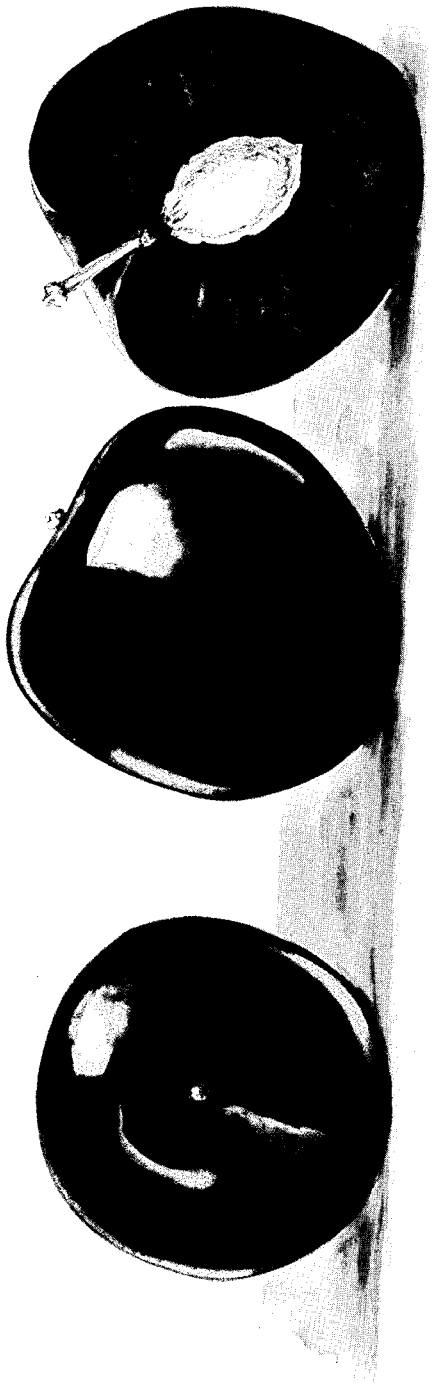
E. W. BURBANK
Executrix of
LUTHER BURBANK, deceased
By Cobb & Cobb
Attorneys Patented Apr. 5, 1932

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

PLUM

Application filed September 23, 1930. Serial No. 483,936.

This invention relates to a new and distinct variety of plum.

This new creation is an astonishingly large and beautifully colored variety of deep carmine plum, which, when mature, becomes tender and melting; its mild, refreshing, subacid flavor adds effectiveness to its merits. A cross section of this plum quite definitely resembles a heart; the base and stem end half because of its symmetry, seems to adhere to the heart shape with marked precision, while the form varies only slightly at the apex. The tree is very hardy. The fruit, though thin skinned, does not easily become damaged, for the flesh is firm, becoming tender with maturity.

The annexed drawings and specification to follow present the distinctions and characteristics of the variety of plum which has been asexually reproduced.

*Full grown trees*

*Tree.*—The tree's growth is vigorous; branches upright, somewhat irregular and developing an open structure for the head of the tree. The branches are stiff and strong; forks acute, angle about 45 degrees, strongly knit. The older bark is dark gray, roughened by longitudinal cracks exfoliating sparingly in flakes.

*Foliage.*—The mature leaves of normal new growth are large to very large, measuring about 5 inches long and 2½ inches wide. The leaves on the strongest shoots are immense in size, measuring about 6 inches long and 4 inches wide. The leaf form is ovate to elongated oval. The texture is medium to heavy, with the older leaves becoming leathery but not harsh. The upper surface is smooth, moderately glossy and dark green in color; lower surface is smooth and somewhat glossy. The midrib and veins are prominent, the former being a very light green and having near it a slight pubescence. The base is acute; margin waxy, irregular and double crenate, in some leaves shortened so that the leaf is convex on the upper side. The apex is broadly acute. There are usually two to five well developed glands, reniform, and prominent to the extent of being raised or short stalks or appendages on some leaves.

*Petiole.*—The petiole is medium length, about ⅝ to ¾ inch, and is fairly stout; it is tinged with a dull red on the exposed surface.

*Twigs.*—The new growth twigs have rather long internodes, medium to slender, and are bright green tinged with brownish red. The fruiting spurs are very short-jointed with prominent brown buds. The older twigs develop a distinct gray scarfskin.

*Fruit*

*Form.*—The form is roundish oval tending toward round-cordate. The size is very large, the axial diameter measuring about 2⅜ inches long; largest transverse diameter 2¼ inches and the smaller transverse diameter is about 2⅛ inches. The stem is medium to short measuring about ⅝ inch in length and is rather slender in proportion to size of fruit, slightly enlarged at insertion. Its color is green with brown markings. The cavity is wide and of medium depth, descending abruptly to insertion of stem. It is characterized by tendency to show distinct, very narrow concentric cracks about the stem end. The suture begins at the stem, is distinct becoming more shallow and ending at the apex which is barely noticeable.

*Color.*—The skin is a deep carmine, shading to blackish red-purple over the larger part of the fruit. There are yellowish dots, submerged, and disappearing in the deep coloring. The bloom is thin and readily rubbed off.

*Skin.*—The skin is thin and adheres to the flesh but permits removal with slight effort. The surface becomes waxy with maturity.

*Stone.*—The stone is free and is small for the large size of the fruit, being about 1 inch long including point, ¾ inch wide and ⅜ inch thick. The form is ovate. The dorsal side is largest due to prominent ridges which are almost winged. The ventral suture is a deep groove, distinctly notched. Both sides are slightly pitted. The stone color is light buff, and when fruit is fully ripe is stained pink.

*Flesh.*—The flesh is a deep red purple uniformly shaded from skin to pit. The flesh is firm until mature, then it becomes tender and melting. It is very juicy, with a mild, refreshing, subacid, aromatic and pleasing flavor.

The specifications above, and attached drawing, manifest the general characteristics of the plum, yet it is understood they may vary slightly due to climatic conditions.

What is claimed is:

The plum tree herein described, characterized by the early ripening period of its fruit, as shown.

In testimony whereof I affix my signature.

ELIZABETH WATERS BURBANK,
*Known also as Elizabeth Burbank, Executrix of Luther Burbank, Deceased.*